(12) United States Patent
Sadotomo et al.

(10) Patent No.: US 7,623,619 B2
(45) Date of Patent: *Nov. 24, 2009

(54) X-RAY CT APPARATUS

(75) Inventors: Tetsuya Sadotomo, Tochigi-ken (JP); Makoto Nakano, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/964,508

(22) Filed: Dec. 26, 2007

(65) Prior Publication Data

US 2008/0159470 A1    Jul. 3, 2008

(30) Foreign Application Priority Data

Dec. 22, 2006    (JP)    ............................ P2006-345822

(51) Int. Cl.
*G01N 23/00*    (2006.01)

(52) U.S. Cl. .............................. 378/15; 378/4; 378/193; 378/197

(58) Field of Classification Search ..................... 378/4, 378/9, 15, 17, 193, 195, 196, 197, 210
See application file for complete search history.

(56) References Cited

U.S. PATENT DOCUMENTS 7,291,840 B2 * 11/2007 Fritzler et al. .......... 250/363.05
2007/0274436 A1 * 11/2007 Harada et al. .................. 378/15

FOREIGN PATENT DOCUMENTS

JP    2003-079608    3/2003

* cited by examiner

*Primary Examiner*—Jurie Yun
(74) *Attorney, Agent, or Firm*—Oblon, Spivak, McClelland, Maier & Neustadt, L.L.P.

(57) ABSTRACT

An X-ray CT apparatus that achieves a higher quality of reconstructed CT images by preventing displacements of relative positions of the X-ray tube and the X-ray detector from occurring, including a front side rotation frame configured to mount at least one X-ray tube and at least one X-ray detector facing the X-ray tube, and a rear side rotation frame configured to mount rotation units other than the X-ray tube and the X-ray detector in order to access both sides of the gantry.

12 Claims, 5 Drawing Sheets

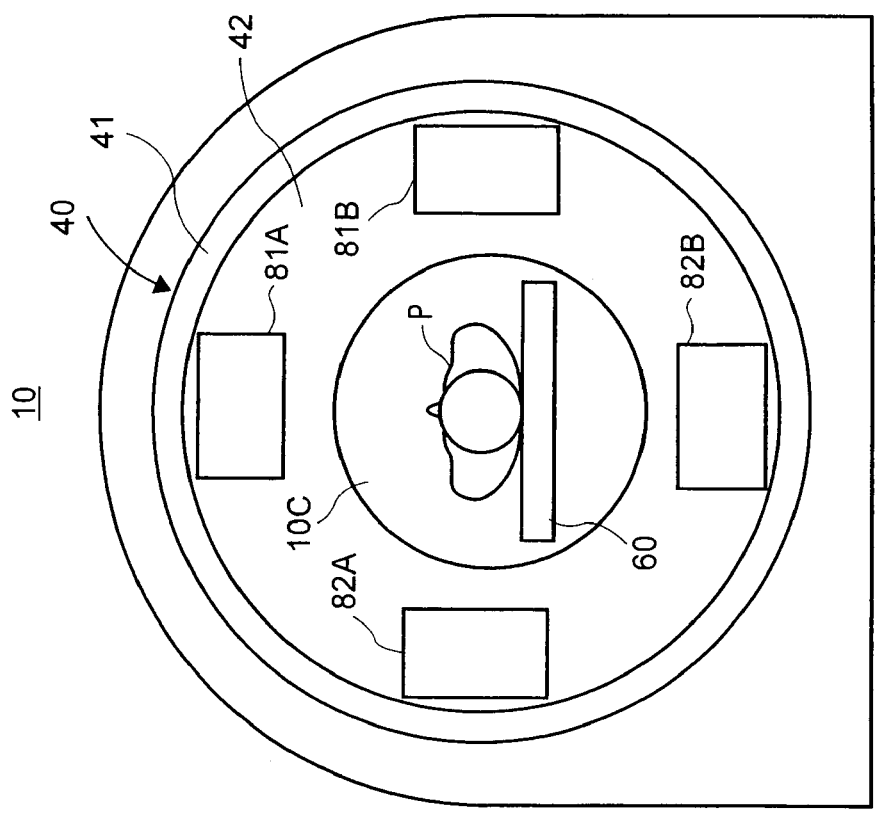
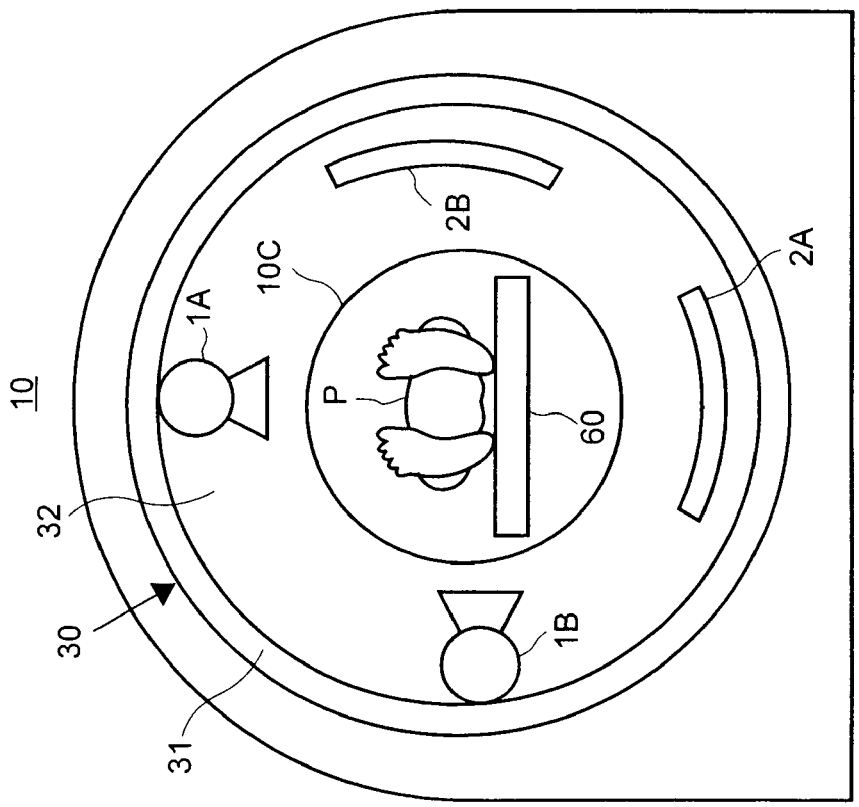

X-RAY CT APPARATUS

CROSS-REFERENCE TO RELATED APPLICATIONS

This application claims priority from, and the benefit of, Japanese Patent Application No. 2006-345822, filed on Dec. 22, 2006, the contents of which are expressly incorporated herein by reference in their entirety.

BACKGROUND OF THE INVENTION

1. Field of the Invention

The present invention relates to an X-ray computer tomography (CT) apparatus, and more particularly, to a rotation frame configuration in a gantry suitable for a multi-X-ray tube type X-ray CT apparatus.

2. Background of the Invention

In an X-ray CT imaging apparatus having a multi-slice detector, an X-ray source irradiates a fan-shaped X-ray beam through an object and X-ray amounts penetrated through the object are detected by each element of the detector provided opposite the X-ray source. Corresponding detected projection data from the detection are reconstructed in order to display tomography images. A two dimensional multi-slice detector including a plurality of channels along a traversing direction (x-axis) of the object has a z-axis corresponding to an image slice (row) direction so as to form an arc shaped configuration in a direction traversing z-axis. An X-ray source and a multi-slice detector are provided in a gantry so as to be located at positions opposite each other and are rotated around an object placed at a center position of the gantry. By rotating an X-ray source and a multi-slice detector around an object in different angles, a series of views are obtained. This operation is referred to as a "scan".

An X-ray CT apparatus reconstructs tomography images based on projection data acquired by scanning an object from various directions. Thus, an X-ray CT apparatus acquires projection data from various directions by rotating X-ray source around the object. Usually, an X-ray CT apparatus includes a rotation frame in a gantry for supporting an X-ray tube, a detector positioned so as to face the X-ray tube and a high voltage generating apparatus for supplying a high voltage to the X-ray tube located inside of the rotation frame. The rotation frame is fixed to a main frame through main bearing units.

Recently, in accordance with development of small-sized light-weight X-ray tubes, a multi-tube type X-ray CT apparatus has been developed for supporting a plurality of X-ray tubes and a plurality of X-ray detectors in a rotation frame. Such a multi-tube type X-ray CT apparatus is, for instance, suggested in a Japanese Patent Application Publication 2003-79608. The multi-tube type X-ray CT apparatus includes a plurality of X-ray tubes and a plurality of X-ray detectors that respectively face each other in a same plane. Accordingly, the scanning time required to acquire projection data necessary to reconstruct one tomography image is shortened, since projection data on the same slice plane from various directions can be acquired. In particular, such a multi-tube type X-ray CT apparatus is effective in diagnosis of a circulatory organ, such as a heart.

The multi-tube type X-ray CT apparatus above described needs to support various rotation units including a plurality of X-ray tubes, a plurality of X-ray detectors facing the plurality of X-ray tubes and a plurality of high voltage generating units for supplying a high voltage to each of the plurality of X-ray tubes in a rotation frame. Consequently, it becomes impossible to support such multiple rotation units in the same sized rotation frame as that of a conventional single tube type X-ray CT apparatus. Furthermore, a predetermined distance (X-ray path) must be kept between an X-ray source that includes a X-ray tube and a collimator for focusing irradiated X-rays (hereinafter, simply referred to as "an X-ray tube" and an X-ray detector positioned so as to face the X-ray tube. Thus, it is required to support these various rotation units without enlarging a diameter of the rotation frame.

Consequently, a conventional multi-tube type X-ray CT apparatus employs a rotation frame configuration 5 as shown in FIG. 5. Similar to the configuration of a single tube type X-ray CT apparatus, the rotation frame 100 is supported by the main frame 101 through main bearing units. In a multi-tube type X-ray CT apparatus, in order to mount many rotation units on the rotation frame, a circular ring member of the rotation frame 100 is horizontally extended along a rotation axis O in a bed side direction, i.e., a front-side direction of the gantry, from the main frame 101. As shown in FIG. 5, all of the rotation units 106 including a plurality of X-ray tubes 104, a plurality of X-ray detectors 103, a plurality of high voltage generating units 105 and other rotation units are mounted on the inner side of the extended member of the rotation frame 100 in one direction from the main frame 101.

In order to facilitate positioning of X-ray irradiation through an object, a plurality of X-ray tubes 104 and a plurality of X-ray detectors 103 are mounted on the extended member of the rotation frame 100 at a position near the bed apparatus. A plurality of high voltage generating apparatuses 105 for supplying a high voltage to each of the X-ray tubes and other rotation units 106 are arranged at a rear (back) side position of the plurality of X-ray tubes 104 and the plurality of X-ray detectors 103, i.e., a position near to the main bearing units 102. Thus, all of many rotation units are concentrated on the extended member of the rotation frame 100. Consequently, the rotation center of gravity G of the rotation frame 100 in the gantry is displaced from the rotation center of the main bearing units 102 and shifted in the bed apparatus direction, i.e., a front-side direction.

As a result, in order to support the rotation frame 100 and the main frame 101, the moment load added to the main bearing units 102 is greatly increased compared to the moment load to bearing units in a gantry for a single tube type X-ray CT apparatus. This generates a problem that the life of main bearing units 102 becomes short compared with that of the single tube type X-ray CT apparatus. Further, each of positions of X-ray paths from an X-ray tube 104 and an X-ray detector 103 is also shifted in a bed apparatus direction, i.e. a front side direction from the rotation center of the main bearing units 102. Accordingly, a deformation amount of the rotation frame 100 due to the rotation gravity G becomes large during a high speed rotation of the rotation frame 100. Such deformation causes divergences of the X-ray paths so that quality of reconstructed images deteriorates. Furthermore, when exchange of rotation units mounted at a rear side, i.e., near to the main bearing units 102, such as the high voltage generating apparatus 105, is needed for maintenance, it is necessary to remove the rotation unit mounted on the front (bed) side, such as the X-ray tube 104 in order to access the rear side rotation units. Since the access operability for the maintenance becomes complicated, the down time of the system also increases, which is also a problem of the conventional multi-tube type X-ray CT apparatus.

SUMMARY OF THE INVENTION

The present invention addresses the abovementioned problems and defects of the conventional X-ray CT apparatus. The present invention provides a new multi-tube type X-ray apparatus that can contain distortions of a rotation due to high speed rotation in order to decrease the moment load added to the bearing units and prolong the life of bearing units. Further, the present invention provides a new multi-tube type X-ray apparatus that can avoid the divergences of X-ray paths between X-ray sources and X-ray detectors in order to prevent occurrence of deteriorations of quality of reconstructed images. Furthermore, the present invention provides a new multi-tube type X-ray apparatus capable of providing early access to rotation units for maintenance in a short time so as to reduce the down time the system.

Thus, the multi-tube X-ray CT apparatus consistent with the present invention includes a rotation frame providing at least one X-ray tube and at least one X-ray detector facing the X-ray tube at a front side, i.e., a bed side, bearing units that become a rotation center, and other rotation units other than the X-ray tube and the X-ray detector, such as a plurality of high voltage generating units, provided at a rear side, i.e., a counter bed side of the bearing units. Thus, a plurality of rotation units necessary for the multi-tube type X-ray CT apparatus are mounted on both the front side and the back side of the bearing units to distribute weight substantial equally on either side of the bearing units.

According to one aspect of the present invention, there is provided an X-ray CT apparatus including a front-side rotation frame configured to mount at least one X-ray tube for irradiating X-rays over an object and at least one X-ray detector provided at a position facing the X-ray tube in order to detect the irradiated X-rays through an object;

a rear-side rotation frame configured to mount at least one other rotation unit other than the at least one X-ray tube and the at least one X-ray detector, including at least one high voltage generating unit for supplying a high voltage to the at least one X-ray tube;

a main frame configured to support the front-side rotation frame and the rear-side rotation frame;

at least one bearing unit provided on a circular surface of the main frame at a position between the front-side rotation frame and the rear-side rotation frame so as to form a smaller major diameter than the diameter of the respective side of the rotation frame; and a frame coupling portion configured to couple the front-side rotation frame and the rear-side rotation frame to the plurality of bearing units.

According to another aspect of the present invention, there is provided an X-ray CT apparatus including:

a circular rotation frame;

a plurality of bearing units provided so as to surround an outer surface of the circular rotation frame; and a circular main frame configured to support the circular rotation frame through the plurality of bearing units;

wherein the circular rotation frame includes, a front-side annular member configured to mount at least one X-ray tube for irradiating X-rays over an object and at least one X-ray detector provided at a position facing to the X-ray tube in order to detect the irradiated X-rays through an object, a rear-side annular member configured to mount at least one high voltage generating unit for supplying a high voltage to the at least one X-ray tube and rotational units other than the at least one X-ray tube and the at least one X-ray detector, and a vertical rib member projected from a surface of a connecting portion of the front-side annular member and the rear-side annular member toward a rotation axis of the rotation frame, the vertical rib member has a center aperture.

BRIEF DESCRIPTION OF THE DRAWINGS

The accompanying drawings, which are incorporated in and constitute part of this specification, illustrate various embodiments and/or features of the present invention, and together with the description, serve to explain the present invention. Where possible, the same reference number will be used throughout the drawings to describe the same or like parts. In the drawings:

FIG. 3A is a front-side (bed side) view of the embodiment of the rotation frame in the gantry shown in FIG. 2.

FIG. 3B is a rear-side (counter-bed side) view of the embodiment of the rotation frame in the gantry shown in FIG. 2.

DETAILED DESCRIPTION OF THE PREFERRED EMBODIMENTS

With reference to the following FIGS. 1-4, embodiments consistent with the present invention will be explained. Usually, a multi-tube type X-ray CT apparatus includes a plurality of X-ray tubes. For better understanding, as an exemplary embodiment of a multi-tube type X-ray CT apparatus consistent with the present invention, a multi-tube type X-ray CT apparatus simply having two X-ray tubes will be explained. Each of two X-ray tubes are to be supplied a high voltage from two high voltage generating units, respectively.

Figure 1:
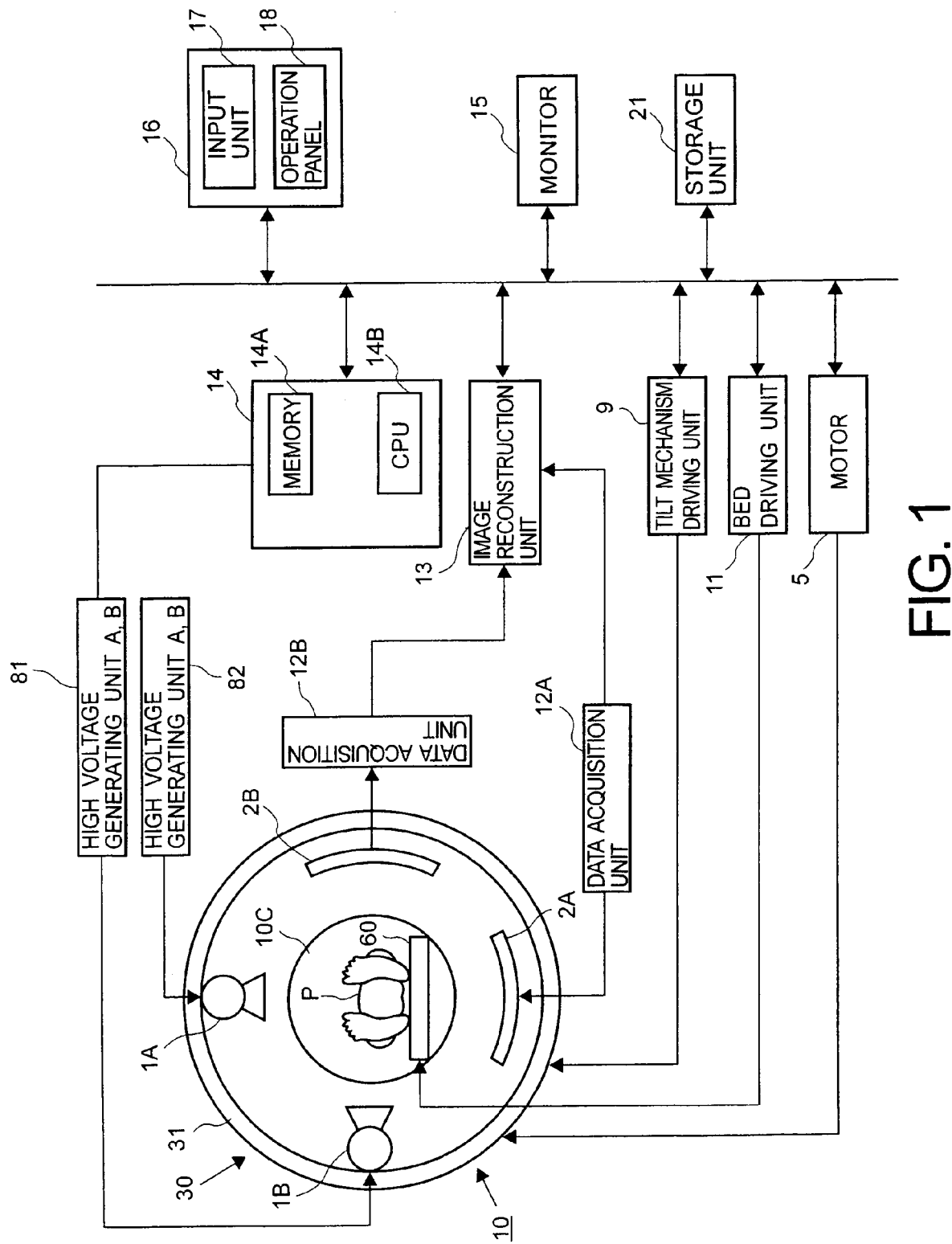
FIG. 1 is a block diagram illustrating a construction of an X-ray CT apparatus consistent with one embodiment of the present invention.

FIG. 1 shows a block diagram of the construction of the multi-X-ray tube type CT apparatus 100X having a gantry 10 including a rotation frame 30 of a configuration consistent with the present invention. The multi-tube type X-ray CT apparatus 100X includes a bed apparatus (not shown) having a top plate 60 for supporting an object P, a gantry unit 10 including a rotation frame 30 configured to rotate a plurality of X-ray tubes 1A, 1B and a plurality of X-ray detectors such as, for instance, two-dimensional multi-slice X-ray detectors 2A, 2B positioned so as to face the plurality of X-ray tubes 1A, an image reconstruction unit 13 configured to reconstruct X-ray CT images of the object P based on projection data by performing a prescribed image reconstruction process, and a monitor 15 configured to display the reconstructed X-ray CT images. Thus, when an object P supported on a top plate 60 of the bed apparatus is inserted into a central aperture portion 10C of the gantry, an X-ray, such as a fan-beam X-ray is irradiated from each of the plurality of X-ray tubes 1A, 1B by supplying a high voltage from the plurality of generating units 81, 82. X-rays penetrated through the object are collected through the plurality of two dimensional multi-slice X-ray detectors 2A, 2B positioned so as to face the plurality of X-ray tubes 1A, 1B. The X-ray amount penetrated through each of the X-ray detectors 2A, 2B is collected by a plurality of data acquisition units 12A, 12B as projection data and supplied to the image reconstruction unit 13 in order to produce X-ray CT images by performing a prescribed image reconstruction process. The X-ray CT images are displayed on the monitor 15 and stored in a storage unit 21 based on controls of a control unit 14.

In this embodiment, projection data are collected by rotating the rotation frame 30 mounting the plurality of X-ray tubes 1A, 1B and the plurality of X-ray detectors 2A, 2B at high speed together with moving the top plate 60. Of course, it is possible to collect projection data generated from a plurality of X-ray tubes through at least one X-ray detector.

When operation data, such as scan conditions, are inputted through an input apparatus 17 in a console 16, a CPU 14B in a control unit 14 executes various programs that are in advance read in a memory 14A in a control unit 14. The control unit 14 provides various control signals to each of various gantry units. For instance, the control unit 14 supplies control signals to high voltage generating units 81 and 82 in order to generate a high voltage. By supplying the high voltage to the each of the X-ray tubes 1A and 1B, X-ray beams, such as fan-shaped beams, are irradiated onto the object. In this embodiment, it is supposed that two high voltage generating units supply each of high voltages to one X-ray tube. Thus, it is supposed that the X-ray tube 1A receives high voltages from the high voltage generating unit 81A and the high voltage generating unit 81B. Similarly, it is supposed that the X-ray tube 1B receives high voltages from the high voltage generating unit 82A and the high voltage generating unit 82B.

The top plate 60 provided on a bed apparatus supports the object P in order to move the object P along a body axis direction and also move up and down by operating panel 18 provided in a console 16. When operation data is supplied through a bus line based on the operation of the operation panel 18, control signals from the CPU 14B in the control unit 14 are supplied to a bed driving unit 11. Based on the drive signals from the bed driving unit 11, the top plate 60 on the bed apparatus can be moved as instructed. When the object P is placed at a predetermined position in a center aperture 10C in the gantry by moving the top plate 60, operation data is supplied from the operation panel 18 through a bus line in order to drive a motor 5. When the motor 5 is driven based on the control signals supplied from the CPU 14B in the control unit 14, a front side rotation frame 30 that supports the X-ray tubes 1A and 1B and the X-ray detectors 2A and 2B provided so as to face the X-ray tubes 1A and 1B is rotated in a high speed. As explained later, a rear side rotation frame 40 is also rotated in a high speed together with the front side rotation frame 30. Thus, the front rotation frame 30 and the rear rotation frame 40 are rotated in a high speed as a unitary body. Further, it is possible to tilt the unitary body of the rotation frame against a body axis of the object P during a high speed rotation. Tilting drive of the rotation frame is performed based on tilt rotation data supplied from the operation panel 18 through the bus line. Thus, based on the tilt rotation data, the control signals supplied from the CPU 14B in the control unit 14 drive a tilt mechanism driving 5 that couples the rotation frame and a gantry stand (88 shown in FIG. 4). By driving the tilt driving mechanism, of the entire rotation frame rotates around the object P at a prescribed tilting angle against the body axis.

As explained above, the operation unit 16 performs input operation for giving instructions to move the gantry 10 and the top plate 60 of the bed apparatus. Further, the operation unit 16 instructs to start irradiation of X-rays. The operation unit 16 includes an input apparatus 17 for inputting, for example, characters and/or numerals, and an operation panel 18 for instructing various driving operations. In accordance with input operations through the operation panel 18, control signals for performing rotation drives or tilt drives of the rotation frame and up and down or horizontal drives of the top plate are supplied from the CPU 14B in the control unit. The motor 5, the high voltage generating units 81 and 82, the tilt mechanism driving unit 9 and the bed driving unit 11 are controlled based on the control signals. An opposed pair of an X-ray tube 1 and an X-ray detector 2 that are mounted on the rotation frame is rotated around a body axis of an object P inserted at a predetermined position in the center aperture 10C of the gantry. Thus, X-rays irradiated from the X-ray tube penetrate through the object and are detected by the X-ray detector as projection data.

Figure 2:
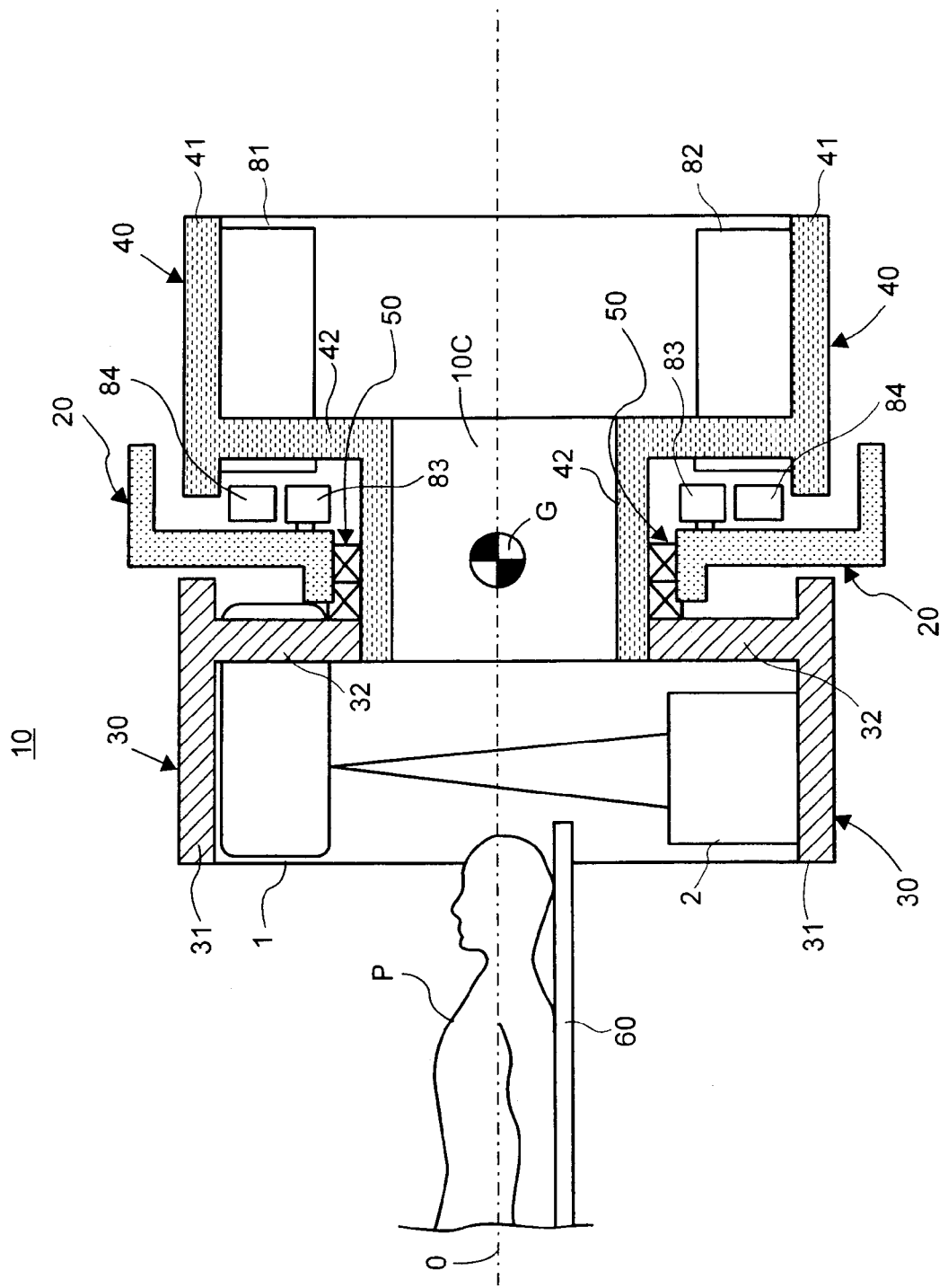
FIG. 2 is a cross-sectional view of a construction of one embodiment of the rotation frame in a gantry of the X-ray CT apparatus shown in FIG. 1.

FIG. 2 illustrates a cross-sectional view of one embodiment of the rotation frame in a gantry configuration suitable for a multi-tube type X-ray CT apparatus consistent with the present invention. The rotation frame in the gantry 10 includes a circular main frame 20 that is fixed to a floor through a gantry stand (not shown), a front-side rotation frame 30 that is coupled to the main frame 20 through main bearing units 50 and a rear-side rotation frame 40. The front-side rotation frame 30 is constructed by a circular front horizontal member 31 that horizontally extends from the main frame 20 in a direction to the bed apparatus along a rotation axis O and a circular front-side wall member 32 that vertically extends from a main frame side edge portion of the circular front horizontal member 31 in a direction to the rotation axis O. The front-side rotation frame 30 and the rear-side rotation frame 40 are formed as a unitary body.

Similar to the front-side rotation frame 30, the rear-side rotation frame 40 is constructed by a circular front horizontal member 41 that horizontally extends from the main frame 20 in a counter direction to the bed apparatus along a rotation axis O and a circular rear-side wall member 42 that vertically extends from a main frame side edge portion of the circular front horizontal member 31 in a direction to the rotation axis O. In this embodiment, the rear-side rotation frame 40 further includes a horizontal coupling portion that couples an edge portion of the circular rear-side wall member 42 in a direction of the rotation axis and an edge portion of the circular front-side wall member 32 in a direction of the rotation axis. Both edge portions are configured so as to form as a unitary body. Of course, it is also possible to construct the horizontal coupling portion by forming in a unitary configuration with the front-side wall member 32 of the front-side rotation frame 30. Thus, the front-side wall member 32 of the front-side rotation frame 30 and the rear-side wall member 42 of the rear-side rotation frame 40 form a coupling portion through the horizontal coupling portion. Due to the coupling portion, a unitary body of the front-side rotation frame 30 and the rear-side rotation frame 40 can rotate around the rotation axis O of the main frame 20 through the main bearing units 50. The horizontal coupling portion forms a gantry aperture 10C for inserting the object P. The rotation axis O is designed so as to coincide with the body axis of the object P on the top plate 60.

In this embodiment, the front-side rotation frame 30 supports a plurality of X-ray tubes 1A and 1B and a plurality of X-ray detectors, such as two dimensional multi-slice X-ray detectors 2A and 2B which face respective of the respective X-ray tubes 1A and 1B. On the other hand, the rear-side rotation frame 4 supports a plurality of a high voltage generating units 81 and 82 for supplying a high voltage to each of the plurality of X-ray tubes 1A and 1B, and other rotation units 84, such as an oil cooler for cooling the X-ray tubes and transmission control base boards for controlling transmissions of the projection data. Thus, in the present invention, rotation units are separated and provided on both front-side and rear-side directions from the main bearing 50 along the rotation axis O so as to locate the rotation center G of the rotation frame near a rotation center of the main bearing units 50.

A plurality of bearing units are provided on a circular surface of a main frame at a position between the front-side rotation frame and the rear-side rotation frame so as to form a smaller major diameter than the diameter of the respective side of the rotation frame. To rotate a unitary body of the front-side rotation frame 3 and the rear-side rotation frame 4 through the main bearing units 50, a motor 5, shown in FIG. 1, is provided on the main frame 20. Further, a tilt mechanism driving unit (not shown) is provided on a gantry stand for fixing the main frame 20 to a floor in order to perform tilting drives of the unitary main frame 20 of the front-side rotation frame 3 and the rear-side rotation frame 4. The top plate 60 on the bed apparatus can be moved up and down from the body axis of the object P and along the body axis (rotation axis O) by the bed driving unit (not shown).

FIG. 3A is a front-side (bed apparatus side) view of the construction of the rotation frame 10 in the gantry of the X-ray CT apparatus consistent with the present invention such as shown in FIG. 2. The plurality of X-ray tubes 1A and 1B and the plurality of X-ray detectors 2A and 2B are provided on the front-side rotation frame 30 so as to face the object P inserted at a prescribed position in the gantry aperture IC by moving the top plate 60. FIG. 3B is a rear-side (counter bed apparatus side) view of the construction of the rotation frame 10 in the gantry of the X-ray CT apparatus consistent with the present invention such as shown in FIG. 2. For instance, a plurality of high voltage generating units 81A and 81B for supplying a high voltage to the first X-ray tube 1A and a plurality of high voltage generating units 82A, and 82B for supplying a high voltage to the second X-ray tube 1B are provided on the rear-side rotation frame 40. It is also possible to mount data acquisition units on the rear-side rotation frame 40.

In the present embodiment, the rotation frame is explained so as to be applied in a multi-tube type X-ray CT apparatus. Of course, it is possible to apply the rotation frame configuration of the present invention to a conventional single tube type X-ray CT apparatus. Thus, an X-ray tube and an X-ray detector are provided on a front-side rotation frame, and a high voltage generating unit and other rotation units are provided on a rear-side rotation frame in order to be separated from the X-ray tube and an X-ray detector and promote rotational balance.

Figure 4:
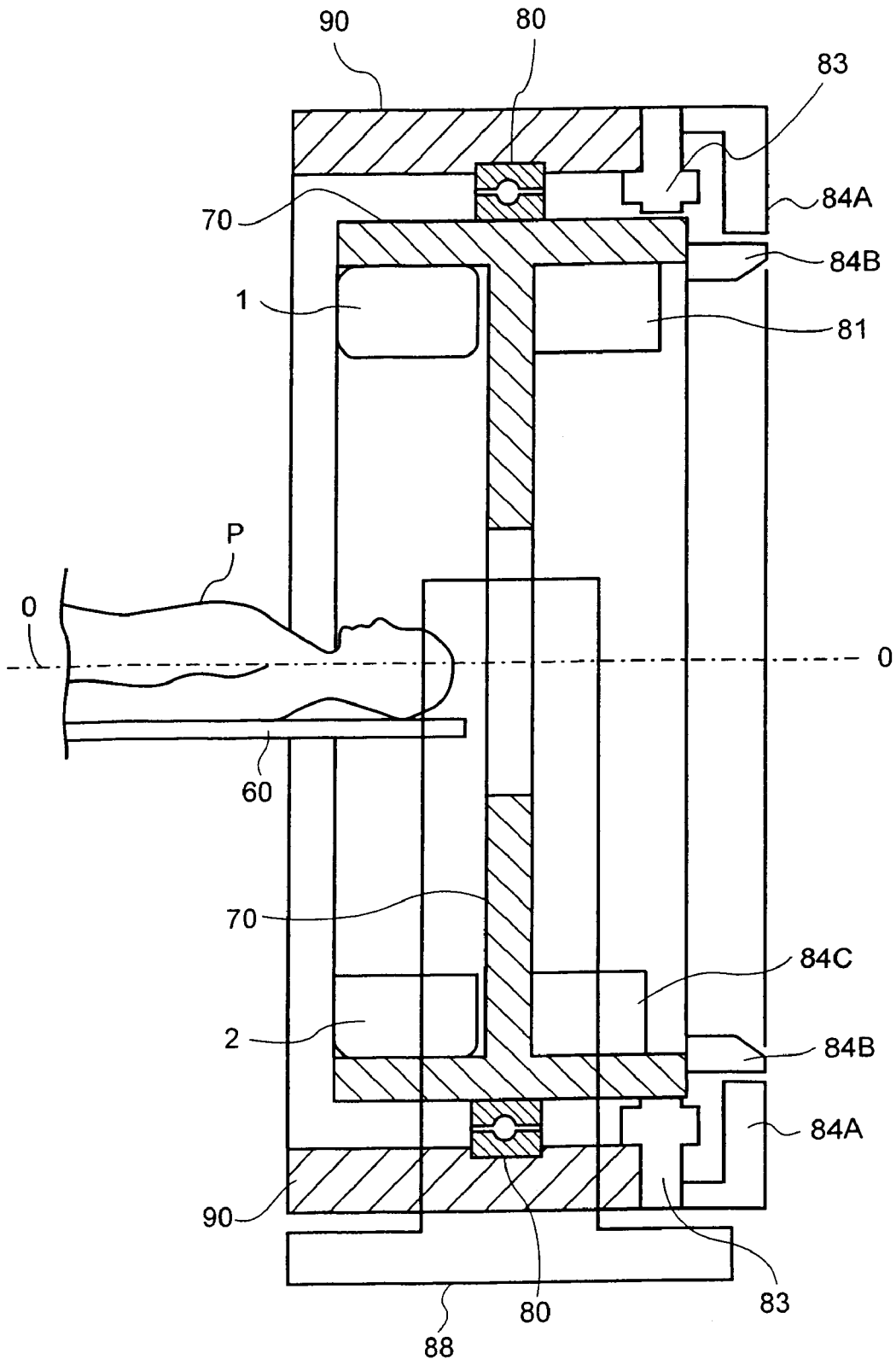
FIG. 4 is a cross-sectional view of a construction of another embodiment of a rotation frame in a gantry of the X-ray CT apparatus consistent with the present invention.
Figure 5:
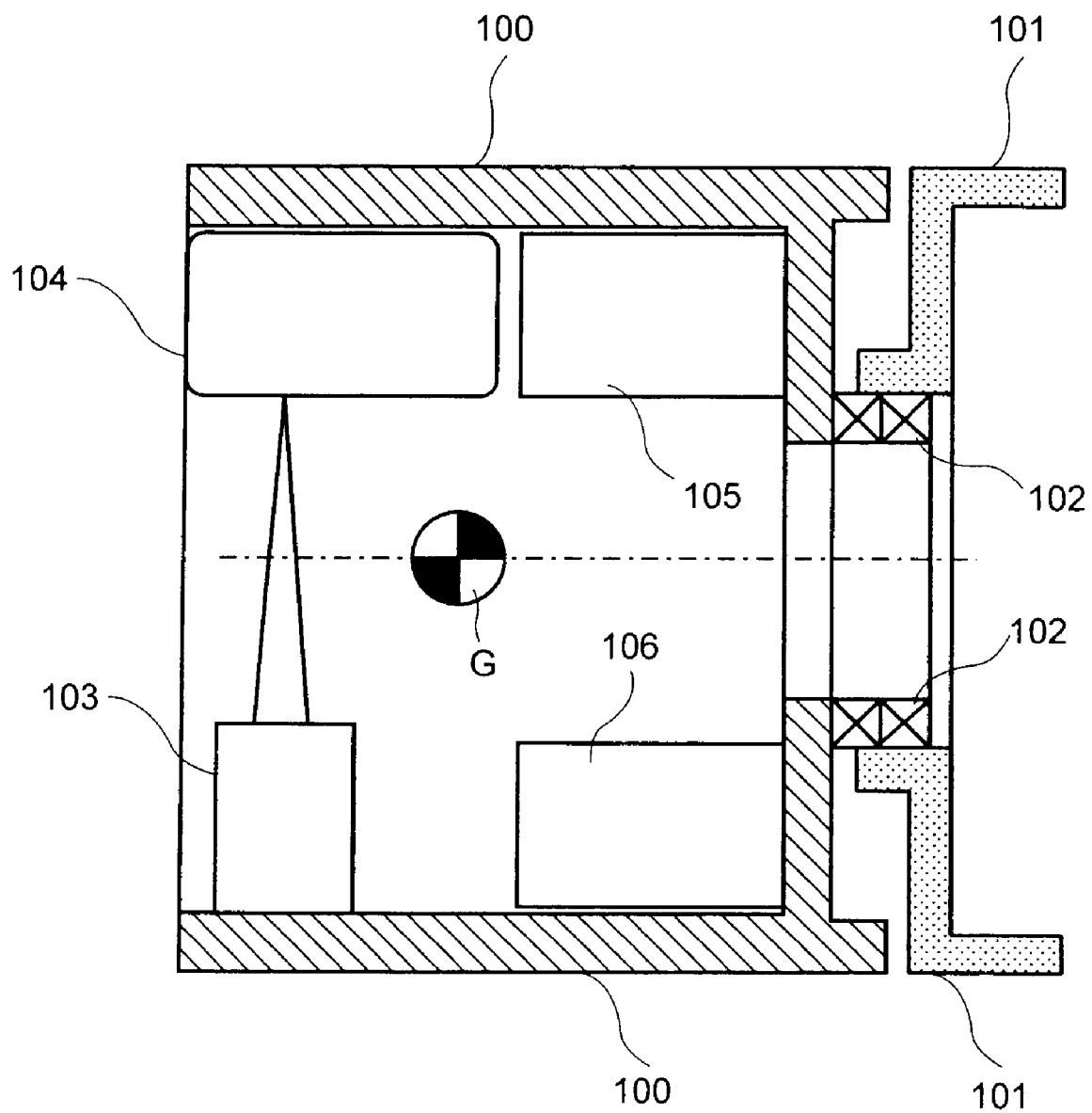
FIG. 5 is a cross-sectional view of a construction of a rotation frame in a gantry for a multi-X-ray tube type X-ray CT apparatus of the background art.

FIG. 4 illustrates another embodiment of a gantry configuration having a circular rotation frame suitable for an X-ray CT apparatus consistent with the present invention. In this embodiment, the circular rotation frame is constructed by an annular ring member and a rib member that is projected from a center position of an inner surface of the annular ring member so as to configure a T-shaped cross-section.

With reference to FIG. 4, another embodiment of a gantry configuration for an X-ray CT apparatus consistent with the present invention will be explained. In this embodiment, the gantry is constructed by a circular rotation frame 70 and a circular fixed frame 90 that is coaxially provided at an outer surface of the circular rotation frame 70. The circular rotation frame 70 is constructed by unifying an annular ring member that extends along a horizontal rotation axis and a rib member projected from a center portion of an inner surface of the annular ring member so as to form a center aperture. Thus, a half cross section of the circular rotation frame 70 along the rotation axis is, as shown in FIG. 4, formed as a T-shaped configuration.

A plurality of main bearing units 80 is provided on an outer surface of the circular rotation frame 70 at substantially equal distances with respect to each other so as to form a ring-like configuration. Further, a circular fixed frame 90 is coaxially provided on the circular rotation frame 70 through the ring-like bearing units 80. The circular fixed frame 90 is fixed to a floor through a gantry stand 88.

In the present embodiment, the circular member of the rotation frame 70 is divided into two portions of a front-side circular part that extends to a bed apparatus side direction from the rib member along the rotation axis and a rear-side circular part that extends to a counter bed apparatus side direction from the rib member along the rotation axis. A front-side circular portion of the circular rotation frame 70 supports a plurality of X-ray tubes 1 for irradiating fan beam X-rays through an object P supported on a top plate 60 of a bed apparatus and a plurality of X-ray detectors 2, such as two dimensional multi-slice X-ray detectors 2 for detecting projection data of the penetrated X-rays through the object P. On the other hand, the rear-side circular portion of the rotation frame 70 supports rotation units other than the X-ray tube and the X-ray detector, for instance, a high voltage generating unit 81 for supplying a high voltage to the X-ray tube 1 and an oil cooler 84C. Usually, power is supplied to the rotation units on the rotation frame 70 through a slip ring.

In this embodiment, in order to rotate the circular rotation frame 70, a motor 83 is provided at a rear-side edge portion of the circular main frame 90 that is fixed to a floor through a gantry stand 88. Further, data transmission members for performing transmission and reception of data are provided on each rear-side edge portions of the circular main frame 90 and of the circular rotation frame 70, respectively. In this embodiment, a fixing-side data transmission member 84A is provided on the rear-side edge portion of the circular main frame 90. A rotation-side data transmission member 84B is provided on the rear-side edge portion of the circular rotation frame 70. The fixing-side data transmission member 84A and the rotation-side data transmission member 84B are respectively formed in a ring-like configuration. The data transmission to and from the fixing-side data transmission member 84A is performed optically by means of light transmission.

In this embodiment, a plurality of rotation units that is necessary for a multi-tube type X-ray CT apparatus are separated and provided in a front side portion of a rib member and a back side of the rib member so as to place a rotation center near to the rib portion. A circular fixed frame 90 is coaxially provided on an outer surface an annular ring member of the rotation frame 70 and an outer surface of the annular ring member of the rotation frame 70 and an inner surface of the circular fixed frame 90 are rotatably supported through a plurality of bearing units 80 arranged in a ring-like configuration. An outer surface of the circular fixed frame 80 is supported by a gantry stand 88 that is fixed on a floor.

The circular fixed frame 90 has a rotation axis coaxial to the rotation axis of the circular rotation frame 70. On one edge of the fixed frame 90 are provided a motor 83 configured to rotate the rotation frame 70 and a fixing side data transmission member 84A configured to perform data transmission and reception operations with a control unit 14 (FIG. 1). Facing the fixing side data transmission member 84A, a rotation side data transmission member 84B for transmitting and receiving data is provided on one edge of the rotation frame 70. The fixing side data transmission member 84A and the rotation side data transmission member 84B are constructed in a ring-like configuration, respectively. Usually, power supply to the rotating units on the rotation frame is performed through a slip ring. The data transmission to and from the fixing side data transmission member 84A and the rotation side data transmission member 84B is performed by means of light transmission.

According to one aspect of the X-ray CT apparatus of the present invention, even when the rotation frame is rotated at a higher speed and the rotation frame receives much larger centrifugal accelerations, displacements of relative positions of the X-ray tube and the X-ray detector can be reduced since the rigidities of the rotation frame along the front side annular member and the rear side annular member are increased and are substantially equal. Consequently, occurrences of displacements of the X-ray paths can be prevented from occurring. Thus, deterioration of reconstructed image can be prevented.

According to an another aspect of the X-ray CT apparatus of the present invention, the plurality of the bearing units can prolong the operational life, since the bearing units are provided between the circular fixed frame and the outer surface of the annular ring member of rotation frame, rotating distortion and moment load added to the bearing units can be reduced. Thus, deterioration of reconstructed image can be prevented.

According to a further aspect of the X-ray CT apparatus of the present invention, it becomes possible to access both a front side and a rear side of the rotation frame, since the rotation units are mounted on the two opposed sides of the annular member of the rotation frame. Consequently, the down time of the system during exchanging operation of the rotation units can be reduced.

As explained above, according to the X-ray CT apparatus of the present invention, the rotational center of gravity of the rotation frame can be maintained near the main bearing units, since a plurality of rotation units are mounted on both a front side and a rear side of the rotation frame. Thus, the moment loads added to the main bearing units can be reduced. Consequently, it becomes possible to prolong the life of the bearing units. It is also possible to use the main bearing units having a smaller rated load, since the moment load added to the main bearing units becomes smaller. Consequently, it becomes possible to reduce the system cost.

According to the X-ray CT apparatus of the present invention, when a maintenance operation is required, it becomes possible to access the rotation units mounted on the rotation frame from both a front side and a rear side of the gantry. Consequently, it becomes possible to exchange only a faulty unit. Thus, efficiencies of maintenance operation can sharply increase and the down time of the system can be minimized.

According to the X-ray CT apparatus of the present invention, the X-ray tubes are mounted at positions near the main bearing units. Consequently, displacements of X-ray paths can be reduced, since distortion of the rotation frame due to the centrifugal acceleration at a higher rotation speed is reduced. Thus, deterioration of a reconstructed image can be prevented.

According to the X-ray CT apparatus of the present invention, tilting imaging operations can be performed by tilting the rotation frame supporting main frame at various angles in a predetermined range of angles while maintaining a rotation center of the rotation frame.

Other embodiments consistent with the present invention will be apparent to those skilled in the art from consideration of the specification and practice of the present invention disclosed herein. It is intended that the specification and examples be considered as exemplary only, with a true scope and spirit of the present invention being indicated by the following claims

The invention claimed is:

1. An X-ray CT apparatus comprising:
 a front-side rotation frame configured to mount at least one X-ray tube for irradiating X-rays through an object and at least one X-ray detector provided at a position facing the X-ray tube in order to detect the irradiated X-rays passing through the object;
 a rear-side rotation frame configured to mount rotation units other than the at least one X-ray tube and the at least one X-ray detector, the other rotation units including at least one high voltage generating unit for supplying a high voltage to the at least one X-ray tube;
 a main frame configured to support the front-side rotation frame and the rear-side rotation frame;
 a plurality of bearing units provided on a circular surface of the main frame at a position between the front-side rotation frame and the rear-side rotation frame and separated so as to form a smaller major diameter than the diameter of the respective side of the rotation frame; and
 a frame coupling portion configured to couple the front-side rotation frame and the rear-side rotation frame to the plurality of bearing units.

2. The X-ray CT apparatus according to claim 1, wherein the front-side rotation frame mounts a plurality of X-ray tubes and at least one X-ray detector facing the plurality of X-ray tubes.

3. The X-ray CT apparatus according to claim 1, wherein the front-side rotation frame mounts a plurality of X-ray tubes and a plurality of X-ray detectors facing respective of the plurality of X-ray tubes.

4. The X-ray CT apparatus according to claim 1, wherein the rear-side rotation frame mounts a plurality of high voltage generating units and rotation units other than the X-ray tube and the X-ray detector.

5. The X-ray CT apparatus according to claim 1, comprising:
 a gantry fixed to a floor and supporting the main frame; and
 a motor configured to rotate the coupled front-side and rear-side rotation frames.

6. The X-ray CT apparatus according to claim 1, further including a tilt driving mechanism for tilting the front-side and rear-side rotation frames at a required angle.

7. An X-ray CT apparatus comprising:
 a circular rotation frame;
 a plurality of bearing units provided so as to surround an outer surface of the circular rotation frame; and
 a circular main frame configured to support the circular rotation frame through the plurality of bearing units;
 wherein the circular rotation frame includes,
 a front-side annular member configured to mount at least one X-ray tube for irradiating X-rays through an object and at least one X-ray detector provided at a position facing the X-ray tube in order to detect the irradiated X-rays passing through the object,
 a rear-side annular member configured to mount at least one high voltage generating unit for supplying a high voltage to the at least one X-ray tube and rotational units other than the at least one X-ray tube and the at least one X-ray detector, and a vertical rib member projected from a surface of a connecting portion of the front-side annular member and the rear-side annular member toward a rotation axis of the rotation frame, the vertical rib member having a center aperture.

8. The X-ray CT apparatus according to claim 7, wherein the front-side annular member of the circular rotation frame mounts a plurality of X-ray tubes and at least one X-ray detector facing the plurality of X-ray tubes.

9. The X-ray CT apparatus according to claim 7, wherein front-side annulus member of the circular rotation frame mounts a plurality of X-ray tubes and a plurality of X-ray detectors facing the plurality of X-ray tubes.

10. The X-ray CT apparatus according to claim 7, wherein the rear-side annular member of the rotation frame mounts a plurality of high voltage generating units and rotation units other than the X-ray tube and the X-ray detector.

11. The X-ray CT apparatus according to claim 7, further comprising:
 a gantry fixed to a floor and supporting the main frame; and
 a motor configured to rotate the front-side annular member and the rear-side annular member.

12. The X-ray CT apparatus according to claim 7, further including a tilt driving mechanism for tilting the rotation frame at a required angle.

* * * * *